(12) United States Patent
Des Jardins et al.

(10) Patent No.: US 11,497,424 B2
(45) Date of Patent: *Nov. 15, 2022

(54) DETERMINATION OF CONTENT SERVICES

(71) Applicant: Comcast Cable Communications, LLC, Philadelphia, PA (US)

(72) Inventors: George Thomas Des Jardins, Washington, DC (US); Scot Zola, Scottsdale, AZ (US); Vikrant Sagar, Silver Springs, MD (US)

(73) Assignee: Comcast Cable Communications, LLC, Philadelphia, PA (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/081,574

(22) Filed: Oct. 27, 2020

(65) Prior Publication Data

US 2021/0106264 A1 Apr. 15, 2021

Related U.S. Application Data

(63) Continuation of application No. 16/436,070, filed on Jun. 10, 2019, now Pat. No. 10,849,542, which is a
(Continued)

(51) Int. Cl.
*G10L 15/26* (2006.01)
*A61B 5/16* (2006.01)
(Continued)

(52) U.S. Cl.
CPC ............ *A61B 5/165* (2013.01); *A61B 5/0022* (2013.01); *A61B 5/4803* (2013.01);
(Continued)

(58) Field of Classification Search
CPC ... A61B 5/165; A61B 6/0022; A61B 2503/12; G16H 40/67; G10I 15/1822; G10L 17/26; G10L 25/63; G10L 25/90
(Continued)

(56) References Cited

U.S. PATENT DOCUMENTS 6,782,551 B1 8/2004 Entwistle
6,925,610 B2 8/2005 Thurston et al.
(Continued)

FOREIGN PATENT DOCUMENTS

EP 1454484 B1 9/2004
EP 1901475 A2 3/2008
(Continued)

OTHER PUBLICATIONS

E. Larson and S. Taulu, "Reducing Sensor Noise in MEG and EEG Recordings Using Oversampled Temporal Projection," in IEEE Transactions on Biomedical Engineering, vol. 65, No. 5, pp. 1002-1013, May 2018, doi: 10.1109/TBME.2017.2734641. (Year: 2018).*
(Continued)

*Primary Examiner* — Bharatkumar S Shah

(74) *Attorney, Agent, or Firm* — Banner & Witcoff, Ltd.

(57) ABSTRACT

According to some aspects, disclosed methods and systems may include having a user input one or more speech commands into an input device of a user device. The user device may communicate with one or more components or devices at a local office or headend. The local office or the user device may transcribe the speech commands into language transcriptions. The local office or the user device may determine a mood for the user based on whether any of the speech commands may have been repeated. The local office or the user device may determine, based on the mood of the user, which content asset or content service to make available to the user device.

44 Claims, 5 Drawing Sheets

Related U.S. Application Data continuation of application No. 14/838,677, filed on Aug. 28, 2015, now Pat. No. 10,362,978.

(51) Int. Cl.
| | | |
|---|---|---|
| *A61B 5/00* | (2006.01) | |
| *G10L 15/18* | (2013.01) | |
| *G10L 17/26* | (2013.01) | |
| *G16H 40/67* | (2018.01) | |
| *G10L 25/63* | (2013.01) | |
| *G10L 25/90* | (2013.01) | |

(52) U.S. Cl.
CPC ........ *A61B 5/6887* (2013.01); *G10L 15/1822* (2013.01); *G10L 17/26* (2013.01); *G16H 40/67* (2018.01); *A61B 2503/12* (2013.01); *G10L 25/63* (2013.01); *G10L 25/90* (2013.01)

(58) Field of Classification Search
USPC ........................................................ 704/235
See application file for complete search history.

(56) References Cited

U.S. PATENT DOCUMENTS

| | | | |
|---|---|---|---|
| 7,509,663 | B2 | 3/2009 | Maynard et al. |
| 7,624,416 | B1 | 11/2009 | Vandermolen et al. |
| 7,680,959 | B2 | 3/2010 | Svendsen |
| 7,757,250 | B1 | 7/2010 | Horvitz et al. |
| 8,095,432 | B1 | 1/2012 | Berman et al. |
| 8,180,804 | B1 | 5/2012 | Narayanan et al. |
| 8,291,321 | B2 | 10/2012 | Matsubayashi |
| 8,302,127 | B2 | 10/2012 | Klarfeld et al. |
| 8,397,257 | B1 | 3/2013 | Barber |
| 8,554,640 | B1 | 10/2013 | Dykstra et al. |
| 8,555,177 | B1 | 10/2013 | Junee et al. |
| 8,677,415 | B2 | 3/2014 | Angiolillo et al. |
| 8,692,763 | B1 | 4/2014 | Kim |
| 8,793,735 | B2 | 7/2014 | VanDuyn et al. |
| 8,856,833 | B2 | 10/2014 | Conness et al. |
| 8,943,529 | B2 | 1/2015 | Kardatzke |
| 9,147,000 | B2 | 9/2015 | Vasudevan et al. |
| 9,183,523 | B2 | 11/2015 | Cudak et al. |
| 9,246,613 | B2 | 1/2016 | McKee et al. |
| 9,247,300 | B2 | 1/2016 | Oddo et al. |
| 9,277,472 | B1 | 3/2016 | Price et al. |
| 9,342,576 | B2 | 5/2016 | Saito et al. |
| 9,407,751 | B2 | 8/2016 | Hansen et al. |
| 9,426,509 | B2 | 8/2016 | Ellis et al. |
| 9,554,163 | B2 | 1/2017 | Ellis et al. |
| 9,832,501 | B2 | 11/2017 | Ruffini et al. |
| 10,034,051 | B2 | 7/2018 | Card, II |
| 2002/0004742 | A1 | 1/2002 | Willcocks et al. |
| 2002/0004748 | A1 | 1/2002 | Koga et al. |
| 2002/0085024 | A1 | 7/2002 | White et al. |
| 2002/0152224 | A1 | 10/2002 | Roth et al. |
| 2002/0152459 | A1 | 10/2002 | Bates et al. |
| 2002/0199188 | A1 | 12/2002 | Sie et al. |
| 2003/0084448 | A1 | 5/2003 | Soundararajan |
| 2003/0145338 | A1 | 7/2003 | Harrington |
| 2003/0233278 | A1 | 12/2003 | Marshall |
| 2004/0031046 | A1 | 2/2004 | Weinblatt et al. |
| 2004/0122736 | A1 | 6/2004 | Strock et al. |
| 2004/0203901 | A1 | 10/2004 | Wilson et al. |
| 2004/0230484 | A1 | 11/2004 | Greenlee |
| 2004/0244030 | A1 | 12/2004 | Boyce et al. |
| 2005/0049858 | A1 | 3/2005 | Busayapongchai |
| 2005/0114340 | A1 | 5/2005 | Huslak et al. |
| 2005/0192000 | A1 | 9/2005 | Lloyd |
| 2006/0031882 | A1 | 2/2006 | Swix et al. |
| 2006/0041478 | A1 | 2/2006 | Zheng |
| 2006/0047678 | A1 | 3/2006 | Miyazaki et al. |
| 2006/0048184 | A1 | 3/2006 | Poslinski et al. |
| 2006/0143236 | A1 | 6/2006 | Wu |
| 2006/0143653 | A1 | 6/2006 | Suh |
| 2006/0149617 | A1 | 7/2006 | Yamashita et al. |
| 2006/0156329 | A1 | 7/2006 | Treese |
| 2006/0176398 | A1 | 8/2006 | Kang |
| 2006/0225088 | A1 | 10/2006 | Gutta |
| 2006/0277100 | A1 | 12/2006 | Parham |
| 2007/0061863 | A1 | 3/2007 | Rajasekaran |
| 2007/0154168 | A1 | 7/2007 | Cordray et al. |
| 2007/0192723 | A1 | 8/2007 | Anzelde et al. |
| 2007/0196795 | A1 | 8/2007 | Groff |
| 2007/0207780 | A1 | 9/2007 | McLean |
| 2007/0294131 | A1 | 12/2007 | Roman et al. |
| 2008/0055272 | A1 | 3/2008 | Anzures et al. |
| 2008/0083001 | A1 | 4/2008 | Peacock et al. |
| 2008/0177617 | A1 | 7/2008 | Gupta |
| 2008/0209229 | A1 | 8/2008 | Ramakrishnan et al. |
| 2008/0243733 | A1 | 10/2008 | Black |
| 2008/0276273 | A1 | 11/2008 | Billmaier et al. |
| 2008/0320139 | A1 | 12/2008 | Fukuda et al. |
| 2009/0019375 | A1 | 1/2009 | Garofalo |
| 2009/0083116 | A1 | 3/2009 | Svendsen |
| 2009/0083779 | A1 | 3/2009 | Shteyn et al. |
| 2009/0089352 | A1 | 4/2009 | Davis et al. |
| 2009/0100463 | A1 | 4/2009 | St. John-Larkin |
| 2009/0119294 | A1 | 5/2009 | Purdy et al. |
| 2009/0132935 | A1 | 5/2009 | Van Zwol |
| 2009/0144635 | A1 | 6/2009 | Miyazaki et al. |
| 2009/0158326 | A1 | 6/2009 | Hunt et al. |
| 2009/0172161 | A1 | 7/2009 | Singh |
| 2009/0216577 | A1 | 8/2009 | Killebrew |
| 2009/0234876 | A1 | 9/2009 | Schigel et al. |
| 2009/0281888 | A1 | 11/2009 | Zai et al. |
| 2009/0300670 | A1 | 12/2009 | Barish |
| 2010/0023506 | A1 | 1/2010 | Sahni et al. |
| 2010/0058376 | A1 | 3/2010 | Alhadeff et al. |
| 2010/0083115 | A1 | 4/2010 | Park |
| 2010/0122207 | A1 | 5/2010 | Kim et al. |
| 2010/0138867 | A1 | 6/2010 | Wong et al. |
| 2010/0162289 | A1 | 6/2010 | Sanders |
| 2010/0229212 | A1 | 9/2010 | Liu et al. |
| 2010/0241699 | A1 | 9/2010 | Muthukumarasamy et al. |
| 2010/0250341 | A1 | 9/2010 | Hauser |
| 2010/0251305 | A1 | 9/2010 | Kimble et al. |
| 2010/0318611 | A1 | 12/2010 | Curtin et al. |
| 2010/0325544 | A1 | 12/2010 | Alhadeff et al. |
| 2010/0325646 | A1 | 12/2010 | Alhadeff et al. |
| 2010/0332330 | A1 | 12/2010 | Goel et al. |
| 2011/0035445 | A1 | 2/2011 | Eickhoff |
| 2011/0124408 | A1 | 5/2011 | Ward |
| 2011/0154213 | A1 | 6/2011 | Wheatley et al. |
| 2011/0161148 | A1 | 6/2011 | Schmidt |
| 2011/0184792 | A1 | 7/2011 | Butcher et al. |
| 2011/0231265 | A1 | 9/2011 | Brown et al. |
| 2011/0264494 | A1 | 10/2011 | Lechowicz |
| 2011/0276882 | A1 | 11/2011 | Buehler et al. |
| 2011/0312375 | A1 | 12/2011 | Kim et al. |
| 2012/0047008 | A1 | 2/2012 | Alhadeff et al. |
| 2012/0064820 | A1 | 3/2012 | Bemmel |
| 2012/0089705 | A1 | 4/2012 | French et al. |
| 2012/0243850 | A1 | 9/2012 | Basra et al. |
| 2013/0046772 | A1 | 2/2013 | Gu et al. |
| 2013/0057765 | A1 | 3/2013 | Zeleznikar |
| 2013/0103628 | A1* | 4/2013 | Skelton .................. G06Q 30/02 706/46 |
| 2013/0125161 | A1 | 5/2013 | Herby et al. |
| 2013/0268966 | A1 | 10/2013 | Foote |
| 2013/0297447 | A1 | 11/2013 | Sakata |
| 2013/0322850 | A1 | 12/2013 | Chang et al. |
| 2013/0325655 | A1 | 12/2013 | Wouhaybi et al. |
| 2014/0019902 | A1 | 1/2014 | DeLuca et al. |
| 2014/0033240 | A1 | 1/2014 | Card, II |
| 2014/0046660 | A1* | 2/2014 | Kamdar ............. G06Q 30/0251 704/235 |
| 2014/0075385 | A1 | 3/2014 | Wan et al. |
| 2014/0123160 | A1 | 5/2014 | van Coppenolle et al. |
| 2014/0130076 | A1 | 5/2014 | Moore et al. |
| 2014/0132524 | A1 | 5/2014 | Lee |
| 2014/0149424 | A1 | 5/2014 | Kalmes et al. |
| 2014/0173435 | A1 | 6/2014 | Arnold |
| 2014/0201766 | A1 | 7/2014 | Stepanov et al. |

(56) References Cited

U.S. PATENT DOCUMENTS

| | | | |
|---|---|---|---|
| 2014/0215506 A1 | 7/2014 | Kalmes et al. | |
| 2014/0331260 A1 | 11/2014 | Gratton | |
| 2015/0003595 A1* | 1/2015 | Yaghi | H04M 3/5175 379/85 |
| 2015/0012416 A1 | 1/2015 | Woods | |
| 2015/0066652 A1 | 3/2015 | Collins et al. | |
| 2015/0089517 A1 | 3/2015 | Ruffini et al. | |
| 2015/0121408 A1 | 4/2015 | Jacoby et al. | |
| 2015/0133164 A1 | 5/2015 | Song et al. | |
| 2015/0143394 A1 | 5/2015 | Hijikata et al. | |
| 2015/0148005 A1 | 5/2015 | Chau et al. | |
| 2015/0169189 A1 | 6/2015 | Want et al. | |
| 2015/0195621 A1* | 7/2015 | Harron | H04N 21/454 725/46 |
| 2015/0199708 A1 | 7/2015 | Ying et al. | |
| 2015/0287219 A1 | 10/2015 | Liang et al. | |
| 2015/0319468 A1 | 11/2015 | Park et al. | |
| 2015/0350709 A1 | 12/2015 | Tomita | |
| 2016/0063998 A1* | 3/2016 | Krishnamoorthy | G10L 15/22 704/254 |

FOREIGN PATENT DOCUMENTS

| | | | |
|---|---|---|---|
| WO | 2007143562 | A2 | 12/2007 |
| WO | 2011002572 | A1 | 1/2011 |

OTHER PUBLICATIONS

M. Schroder et al., "Building Autonomous Sensitive Artificial Listeners," in IEEE Transactions on Affective Computing, vol. 3, No. 2, pp. 165-183, Apr.-Jun. 2012, doi: 10.1109/T-AFFC.2011.34. (Year: 2011).*

Entertainment Fiend: Keep Track of Watched TV Show Episodes and Movies and Plan What to Watch! dated Apr. 11, 2008, http://entertainmentfiend.blogspot.com/2008/04/keep-track-of-watched-tv-show-episodes.html, retrieved Jul. 31, 2014, 4 pages.

Entertainment Fiend: Keep Track of Watched TV Show & Movies and Plan What to Watch—Updated for 2011 Edition, dated Oct. 13, 2011, http://entertainmentfiend.blogspot.com/2011/10/keeping-track-of-watched-tv-shows.html, retrieved Jul. 31, 2014, 2 pages.

Alan Henry. How to Track All Your TV Shows So You Never Miss an Episode, Lifehacker, http://lifehacker/how-to-track-all-your-tv-shows-so-you-never-miss-an-epi-1180239026, 2013, 11 pages.

Thorin Klosowski. Netflix Profiles Ensure Roommates Won't Mess Up Your Recommendations, Lifehacker, http://lifehacker.com/netflix-profiles-ensure-roommates-wont-mess-up-your-re-987927584, dated Aug. 1, 2013, 11 pages.

European Office Action—EP Appl. 11166793.7—dated Oct. 8, 2015.

Canadian Office Action—CA Application No. 2740650—dated Feb. 28, 2017.

European Summons to Oral Proceedings—EP Appl. 11166793.7—dated Apr. 12, 2017.

Feb. 2, 2018—Canadian Office Action—CA 2,740,650.

EP 11166793.9-221 Search Report dated Aug. 5, 2011.

Feb. 21, 2019—Canadian Office Action—CA 2,740,650.

Mar. 12, 2020—Canadian Office Action—CA 2,740,650.

R. Gaglianello, L. Spergel and D. Liu, "Convergence of telephony and television: More than a computer on your TV," 2009 IEEE International Symposium on Broadband Multimedia Systems and Broadcasting, Bilbao, 2009, pp. 1-7, doi: 10.1109/ISBMSB.2009.5133763. (Year: 2009).

J. B. Carlucci, "Social Media Television in Today's Cable Systems," 2010 7th IEEE Consumer Communications and Networking Conference, Las Vegas, NV, 2010, pp. 1-5, doi: 10.1109/CCNC.2010.5421636. (Year: 2010).

D. C. A. Bulterman, P. Cesar, A. J. Jansen, H. Knoche and W. Seager, "Enabling Pro-Active User-Centered Recommender Systems: An Initial Evaluation," Ninth IEEE International Symposium on Multimedia Workshops (ISMW 2007), Beijing, 2007, pp. 195-200, doi: 10.1109/ISM.Workshops.2007.41. (Year: 2007).

P. Cesar, D. C. A. Bulterman and A. J. Jansen, "Social Sharing of Television Content: An Architecture," Ninth IEEE International Symposium on Multimedia Workshops (ISMW 2007), Beijing, 2007, pp. 145-150, doi: 10.1109/ISM.Workshops.2007.34. (Year: 2007).

* cited by examiner 502 504 506

1 f22f7a3b-1e1c-457f-8ff5-3fb1d20fb640 | 2014-01-10 23:17:40 | 400
2 657c2be3-174e-4cee-809e-47b501f31d22 | 2014-01-10 23:17:23 | 61
3 b4491f9b-3e09-4a64-903d-6037182b8854 | 2014-01-10 23:17:01 | watch 400
4 8579e615-2091-4117-8d81-f2c60cc05423 | 2014-01-10 23:16:56 | watch 400
5 23f6069c-9ff8-40db-ba37-08439a66a36e | 2014-01-10 23:16:47 | 400
6 e24e3404-13bc-4251-b2db-8e6c1a3f0243 | 2014-01-10 23:16:34 | 400
7 b0c698e5-f41d-432b-942d-486a155bdb18 | 2014-01-10 23:16:27 | 400
8 1626e5b9-24ac-4c3e-8ed1-6fa1ab26bd2a | 2014-01-10 23:16:23 | 40 car going

FIG. 5

DETERMINATION OF CONTENT SERVICES

CROSS-REFERENCE TO RELATED APPLICATIONS

This application claims priority to and is a continuation of U.S. application Ser. No. 16/436,070, filed Jun. 10, 2019, which claims priority to and is a continuation of U.S. patent application Ser. No. 14/838,677, filed Aug. 28, 2015, now U.S. Pat. No. 10,362,978. Each application is incorporated herein by reference in its entirety and made a part hereof.

BACKGROUND

Content providers have long sought how to determine the mood of a viewer. There is an ever-present need to transmit content or services to a user, while taking into consideration the user's mood.

SUMMARY

The following summary is for illustrative purposes only, and is not intended to limit or constrain the detailed description.

One or more aspects of the disclosure provide for having a user input one or more speech commands into an input device (e.g., microphone, other input device, etc.) of a user device (e.g., set-top box, other computing device, etc.). The user device may communicate with one or more components or devices at a local office or headend. The local office (or the user device) may transcribe the speech commands into language transcriptions. The local office (or the user device) may determine a mood (e.g., angry, happy, etc.) for the user based on whether any of the speech commands may have been repeated (as well as other factors). The local office (or the user device) may determine, based on the mood of the user (or other factors), which content asset or content service to make available to the user device.

One or more aspects of the disclosure provide for a method that may include receiving, by a first device, a first plurality of natural language inputs comprising one or more terms. The method may include assigning a first mood state to a first portion of the first plurality of natural language inputs based on a repetition of one or more of the first plurality of natural language inputs. The method may include transmitting a content service to the first device based on the first mood state.

One or more aspects of the disclosure provide for a method that may include receiving, by a device, a series of commands each associated with accessing content. The method may include determining a mood state associated with the series of commands based on a repetition of one or more of the commands. The method may include providing, based on the mood state, a content feature that is accessible by the device.

One or more aspects of the disclosure provide for a method that may include generating, by a device, a plurality of natural language transcriptions associated with a plurality of natural language inputs, each transcription comprising one or more terms that correlate with one or more terms of a different transcription. The method may include determining a content feature based on a mood state associated with the plurality of natural language transcriptions. The method may include providing the content feature.

The summary here is not an exhaustive listing of the novel features described herein, and is not limiting of the claims. These and other features are described in greater detail below.

BRIEF DESCRIPTION OF THE DRAWINGS

These and other features, aspects, and advantages of the present disclosure will become better understood with regard to the following description, claims, and drawings. The present disclosure is illustrated by way of example, and not limited by, the accompanying figures in which like numerals indicate similar elements.

FIG. 5 illustrates example entries associated with received inputs in accordance with aspects of the present disclosure.

DETAILED DESCRIPTION

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, removable storage media, solid state memory, RAM, magnetic storage devices, or any combination thereof. In addition, the functionality may be embodied in whole or in part in firmware or hardware equivalents, such as integrated circuits, field programmable gate arrays (FPGAs), and the like. Various signals representing data or events as described herein may be transferred between a source and a destination in the form of electromagnetic waves traveling through signal-conducting media such as metal wires, optical fibers, or wireless transmission media (e.g., air or space).

Figure 1:
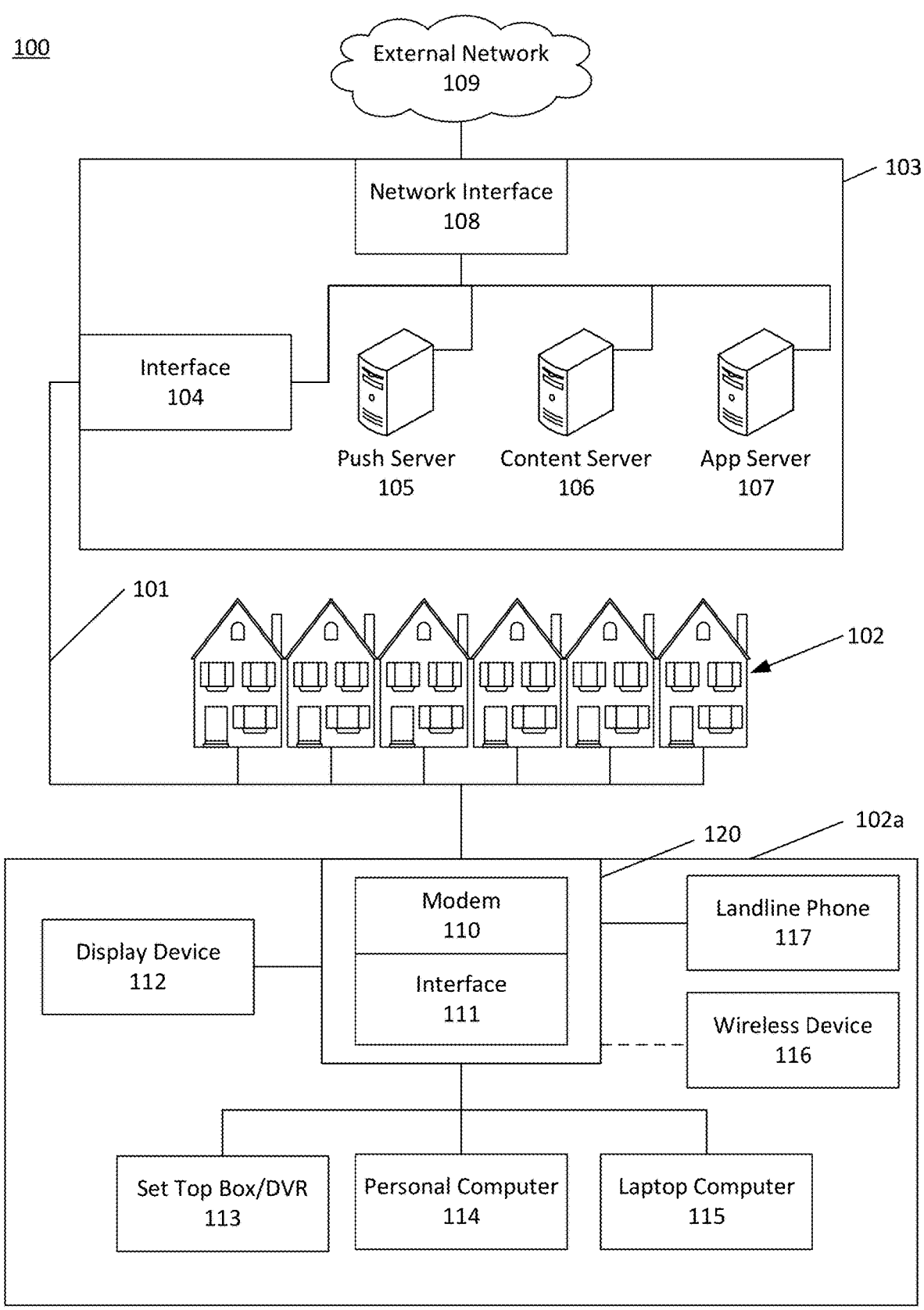
FIG. 1 illustrates an example communication network on which various features described herein may be used.

FIG. 1 illustrates an example communication network 100 on which many of the various features described herein may be implemented. The network 100 may be any type of information distribution network, such as satellite, telephone, cellular, wireless, etc. One example may be an optical fiber network, a coaxial cable network, or a hybrid fiber/coax distribution network. Such networks 100 use a series of interconnected communication links 101 (e.g., coaxial cables, optical fibers, wireless, etc.) to connect multiple premises 102 (e.g., businesses, homes, consumer dwellings, etc.) to a local office or headend 103. The local office 103 may transmit downstream information signals onto the links 101, and each premises 102 may have a receiver used to receive and process those signals.

There may be one or more links 101 originating from the local office 103, and it may be split a number of times to distribute the signal to the various premises 102 in the vicinity (which may be many miles) of the local office 103. The links 101 may include components not illustrated, such as splitters, filters, amplifiers, etc. to help convey the signal clearly, but in general each split introduces a bit of signal degradation. Portions of the links 101 may also be implemented with fiber-optic cable, while other portions may be implemented with coaxial cable, other lines, or wireless communication paths. By running fiber optic cable along some portions, for example, signal degradation may be significantly minimized, allowing a single the local office 103 to reach even farther with its network of the links 101 than before.

The local office 103 may include an interface 104, such as a termination system (TS). More specifically, the interface 104 may be a cable modem termination system (CMTS), which may be a computing device configured to manage communications between devices on the network of the links 101 and backend devices such as the servers 105-107 (to be discussed further below). The interface 104 may be as specified in a standard, such as the Data Over Cable Service Interface Specification (DOCSIS) standard, published by Cable Television Laboratories, Inc. (a.k.a. CableLabs), or it may be a similar or modified device instead. The interface 104 may be configured to place data on one or more downstream frequencies to be received by modems at the various premises 102, and to receive upstream communications from those modems on one or more upstream frequencies.

The local office 103 may also include one or more network interfaces 108, which can permit the local office 103 to communicate with various other external networks 109. These networks 109 may include, for example, networks of Internet devices, telephone networks, cellular telephone networks, fiber optic networks, local wireless networks (e.g., WiMAX), satellite networks, and any other desired network, and the network interface 108 may include the corresponding circuitry needed to communicate on the external networks 109, and to other devices on the network such as a cellular telephone network and its corresponding cell phones.

As noted above, the local office 103 may include a variety of servers 105-107 that may be configured to perform various functions. For example, the local office 103 may include one or more push notification servers 105. The one or more push notification servers 105 may be computing devices that are configured to generate push notifications to deliver data or commands to the various premises 102 in the network (or more specifically, to the devices in the premises 102 that are configured to detect such notifications).

The local office 103 may also include one or more content servers 106. The one or more content servers 106 may be one or more computing devices that are configured to provide content to users at their premises. This content may be, for example, advertisements (such as commercials), video on demand movies, television programs, songs, text listings, etc. The content server 106 may include software to validate user identities and entitlements, to locate and retrieve requested content, to encrypt the content, and to initiate delivery (e.g., streaming or downloading) of the content to the requesting user(s) or device(s). The content server 106 may also be configured to generate advertising decisions and rules, and transmit them to a requesting user or device.

The local office 103 may also include one or more application servers 107. The one or more application servers 107 may be computing devices configured to offer any desired service, and may run various languages and operating systems (e.g., servlets and JSP pages running on Tomcat/MySQL, OSX, BSD, Ubuntu, Redhat, HTML5, JavaScript, AJAX and COMET). In one example, an application server may be responsible for collecting television program listings information and generating a data download for electronic program guide listings. In another example, the application server or another server may be responsible for monitoring user viewing habits and collecting that information for use in selecting advertisements. In yet another example, the application server or another server may be responsible for formatting and inserting advertisements in, for example a video stream being transmitted to the premises 102. The application server or another application server may be responsible for associating interactive components into and with content or advertisements. Although shown separately, one of ordinary skill in the art will appreciate that the push server 105, the content server 106, and the application server 107 may be combined. Further, here the push server 105, the content server 106, and the application server 107 are shown generally, and it will be understood that they may each contain memory storing computer executable instructions to cause a processor to perform steps described herein or memory for storing data.

An example premises 102a, such as a home, may include an interface 120. The interface 120 can include any communication circuitry needed to allow a device to communicate on one or more links 101 with other devices in the network. For example, the interface 120 may include a modem 110, which may include transmitters and receivers used to communicate on the links 101 and with the local office 103. The modem 110 may be, for example, a coaxial cable modem (for coaxial cable lines 101), a fiber interface node (for fiber optic lines 101), twisted-pair telephone modem, cellular telephone transceiver, satellite transceiver, local Wi-Fi router or access point, or any other desired modem device. Also, although only one modem is shown in FIG. 1, a plurality of modems operating in parallel may be implemented within the interface 120. Further, the interface 120 may include a gateway interface device 111. The modem 110 may be connected to, or be a part of, the gateway interface device 111. The gateway interface device 111, such as a gateway, may be a computing device that communicates with the modem(s) 110 to allow one or more other devices in the premises 102a, to communicate with the local office 103 and other devices beyond the local office 103. The gateway interface device 111 may be a set-top box, digital video recorder (DVR), computer server, or any other desired computing device. The gateway interface device 111 may also include (not shown) local network interfaces to provide communication signals to requesting entities/devices in the premises 102a, such as the display devices 112 (e.g., televisions), the additional set-top boxes or the DVRs 113, the personal computers 114, the laptop computers 115, the wireless devices 116 (e.g., wireless routers, wireless laptops, notebooks, tablets and netbooks, cordless phones (e.g., Digital Enhanced Cordless Telephone—DECT phones), mobile phones, mobile televisions, personal digital assistants (PDA), etc.), the landline phones 117 (e.g. Voice over Internet Protocol—VoIP phones), and any other desired devices. Examples of the local network interfaces include Multimedia Over Coax Alliance (MoCA) interfaces, Ethernet interfaces, universal serial bus (USB) interfaces, wireless interfaces (e.g., IEEE 802.11, IEEE 802.15), analog twisted pair interfaces, Bluetooth interfaces, and others.

Figure 2:
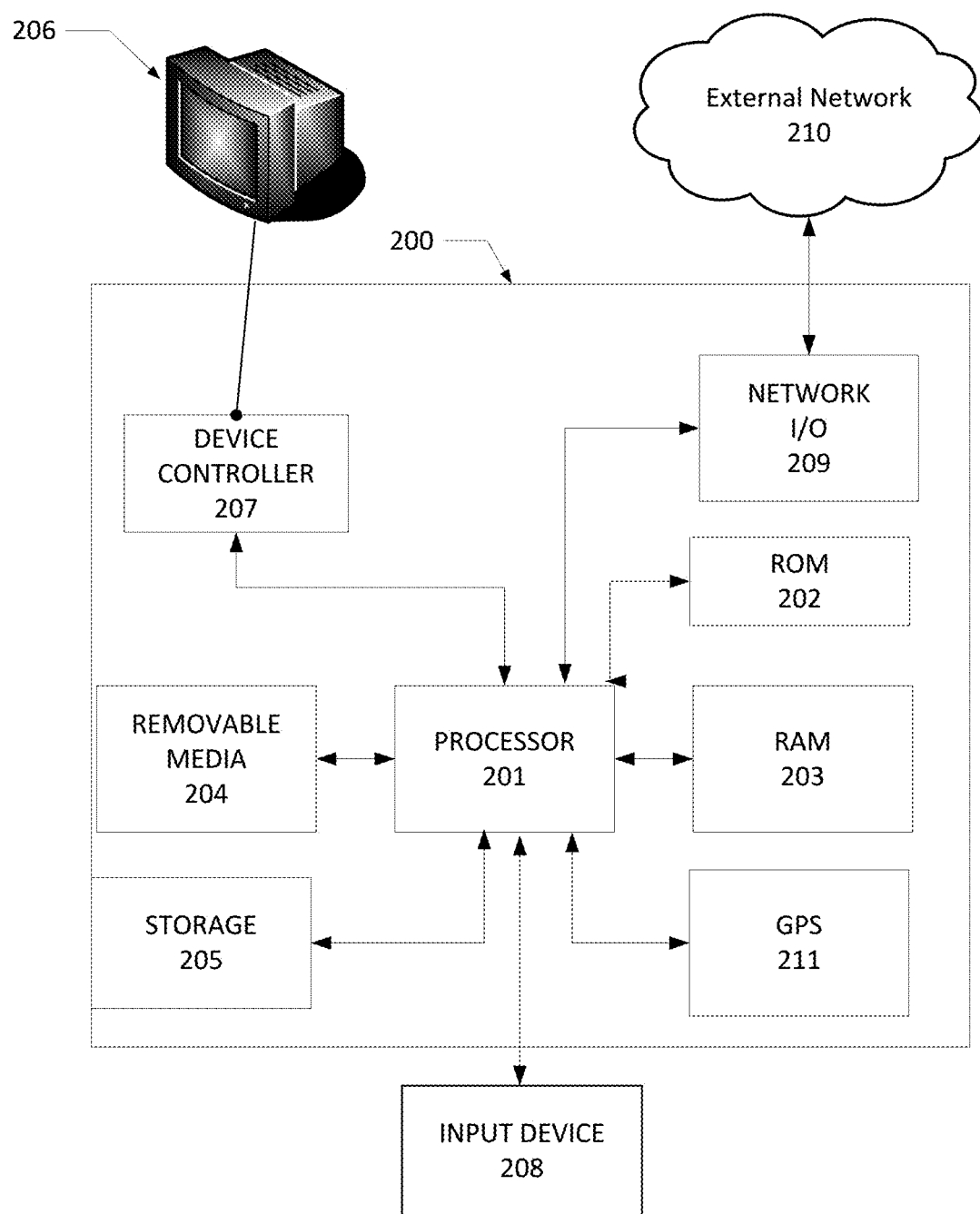
FIG. 2 illustrates an example computing device that can be used to implement any of the methods, servers, entities, and computing devices described herein.

FIG. 2 illustrates general hardware elements that can be used to implement any of the various computing devices discussed herein. The computing device 200 may include one or more processors 201, which may execute instructions of a computer program to perform any of the features described herein. The instructions may be stored in any type of computer-readable medium or memory, to configure the operation of the processor 201. For example, instructions may be stored in a read-only memory (ROM) 202, a random access memory (RAM) 203, a removable media 204, such as a Universal Serial Bus (USB) drive, compact disk (CD) or digital versatile disk (DVD), floppy disk drive, or any other desired storage medium. Instructions may also be stored in an attached (or internal) storage 205, such as a hard drive. The computing device 200 may include one or more output devices, such as a display 206 (e.g., an external television), and may include one or more output device controllers 207, such as a video processor. There may also be one or more user input devices 208, such as a remote control, keyboard, mouse, touch screen, microphone, etc. The computing device 200 may also include one or more network interfaces, such as a network input/output (I/O) circuit 209 (e.g., a network card) to communicate with an external network 210. The network input/output circuit 209 may be a wired interface, wireless interface, or a combination of the two. In some embodiments, the network input/output circuit 209 may include a modem (e.g., a cable modem), and the external network 210 may include the communication links 101 discussed above, the external network 109, an in-home network, a provider's wireless, coaxial, fiber, or hybrid fiber/coaxial distribution system (e.g., a DOCSIS network), or any other desired network. Additionally, the device may include a location-detecting device, such as a global positioning system (GPS) microprocessor 211, which can be configured to receive and process global positioning signals and determine, with possible assistance from an external server and antenna, a geographic position of the device.

FIG. 2 shows an example hardware configuration. Modifications may be made to add, remove, combine, divide, etc., components as desired, and some or all of the elements may be implemented using software. Additionally, the components illustrated may be implemented using basic display devices and components, and the same components (e.g., the processor 201, the ROM 202, the display 206, other input/output devices, etc.) may be used to implement any of the other display devices and components described herein. For example, the various components herein may be implemented using display devices having components such as a processor executing computer-executable instructions stored on a computer-readable medium (e.g., the storage 205), as illustrated in FIG. 2.

Figure 3:
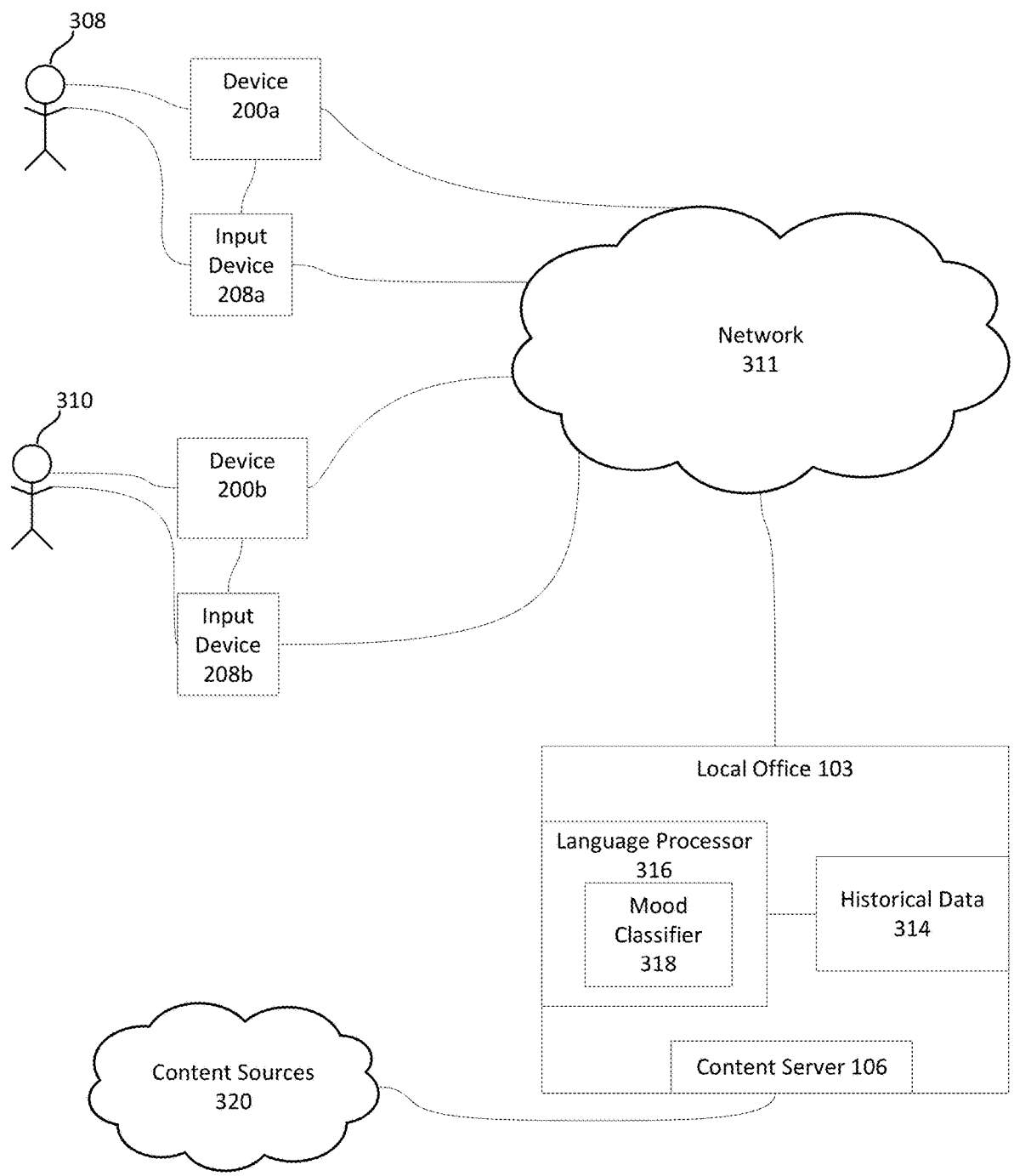
FIG. 3 illustrates an example system in accordance with aspects of the present disclosure.

FIG. 3 illustrates an example system 300 in accordance with one or more disclosed features described herein. The system 300 may include computing devices 200*a* and 200*b*. The computing devices 200*a* and 200*b* may comprise, be substantially similar to, or be the computing device 200, as shown in FIG. 2. The computing devices 200*a* and 200*b* may be any device as shown in FIG. 1. For example, the computing devices 200*a* and 200*b* may be a set-top box 113, personal computer 114, laptop computer 115, gateway 111, modem 110, display device 112, landline phone 117, wireless device 116, a mobile device (smartphone, tablet, smartwatch, Bluetooth device, etc.), digital video recorder (DVR), digital video player, audio device, or any other device capable of providing or accessing media or content, or combinations thereof. The computing devices 200*a* and 200*b* may be operably connected to input devices 208*a* and 208*b*, which may comprise a remote control, keyboard, mouse, touch screen, microphone, or the like used to control and access features of the computing devices 200*a* and 200*b*.

The input devices 208*a* and 208*b* may comprise, be substantially similar to, or be the same as input device 208, as shown in FIG. 2. One or more users, such as user 308 or user 310 may interact with the input devices 208*a* or 208*b* or the computing devices 200*a* and 200*b*. The computing devices 200*a* and 200*b* may be operably connected to the local office 103 via a network 311. The network 311 may comprise, be substantially similar to, or be the same as network 100, link 101, external network 109, or external network 210 as shown in FIGS. 1 and 2. The network 311 may be, for example, a wireless network, a MoCA in-home coaxial cable network, a cellular network, an Ethernet network, a Wi-Fi network, and the like. The local office 103, which may be associated with a head end, may provide content to the computing devices 200*a* and 200*b* via the network 311. As previously shown in FIG. 1, the local office 103 may include one or more content servers 106. The local office 103 (e.g., via the content server 106) may also access and retrieve content from one or more content sources 320, such as internet content sources, music content sources, or video content sources, for transmission to one or more devices, such as the computing devices 200*a* and 200*b*.

Each component of the system 300 may be operably connected to or interact with each other via a direct or indirect connection, such as via a network or hardwire. Each component of the system 300 may be affiliated, operably connected to, or located at a service or content provider, such as the local office 103.

Although FIG. 3 illustrates two computing devices 200*a* and 200*b*, any number of computing devices, such as two, ten, or a hundred, may be included in the system 300 or in any of the embodiments disclosed herein. In one example, the computing devices 200*a* and 200*b* may both be located at the premises 102*a*. In another example, the computing devices 200*a* and 200*b* may be located at separate locations. The computing devices 200*a* and 200*b* may provide or access content services, such as video/image content services, audio content services, internet content services, application (e.g., applications for weather, traffic, music, etc.), and the like, that may be provided by the local office 103. The computing devices 200*a* and 200*b* may access content services and other services via, for example, a video processor or audio processor (for example, similar to device controller 207) and may display content on a display (for example, similar to display 206 as shown in FIG. 2). For example, the computing device 200*a* may launch an application on the computing device 200*a*, and access content via the launched application. The computing devices 200*a* and 200*b* may access content on any number of content platforms, which may include a linear content platform, media (video/audio) on-demand content platform, mobile content platform, a service provider-specific content platform, an online content platform, or other content platform that may be capable of providing content on the computing devices 200*a* and 200*b*, or combinations thereof. For example, the computing devices 200*a* and 200*b* may be mobile devices, and may provide content, such as a movie, through a mobile application. In such a scenario, the content may be provided through a mobile content platform. In another example, the computing devices 200*a* and 200*b* may be set-top boxes, and may provide content, such as a television program or show, via linear content (e.g., live broadcast). In such a scenario, the content may be provided through a linear content platform. In yet another example, the computing devices 200*a* and 200*b* may be set-top boxes, and may provide content, such as a song, using a media on-demand content platform, or may provide content, such as an internet video, using an online content platform. A service provider may provide content that may be specific for that service provider with the service provider's own content platform. For example, content provided on a service provider content platform may be customized by a service provider for a particular computing device or user, such as providing a user's favorite part of a movie, recommended scene of a movie, and the like. Additionally, content provided on a service provider content platform may be a combination of various other platforms, such as combining online content with linear or video on-demand content. The computing devices 200a and 200b may be different types of devices. For example, computing device 200a may be a set-top box, and computing device 200b may be a tablet device.

The users 308 and 310 may access content from the computing devices 200a and 200b. For example, the user 308 may request access to a movie on a set-top box, such as by speaking a command, entering buttons, and the like. The user 308 may then subsequently watch the movie on a display connected to the set-top box. In this example, the user 308 may use an input device 208a (for example, a speech input device or microphone, remote control, eye sensor, motion sensor, etc.) to request access to the movie on the set-top box (for example, the device 200a). The user 310 may also use an input device 208b to request access to content on the device 200b. According to some aspects, the input devices 208a and 208b may be a part of, incorporated in, attached to, or otherwise be connected to devices 200a and 200b. According to some aspects, the input device 208a and 208b may be connected (e.g., directly or indirectly) to the network 311.

The local office 103 may store user identification information for the users 308 and 310 that may be used by the local office 103 to identify user activities. For example, local office 103 may store the name of the user 308 and may use the name as a user ID for the user 308. Accordingly, the local office 103 may identify and store actions of a user (e.g., content selections, what content is accessed, time periods that the user accessed content and did not access content, and the like) using the user ID. According to some aspects, the local office 103 may store device identification information for the devices 200a and 200b that may be used by the local office 103 to identify device activities. For example, the local office 103 may store a name of the device 200a (for example, living room set-top box) and use the name as a device ID for device 200a. The local office 103 may then identify and store actions of a device, similar to the above user ID example.

According to some aspects, the local office 103 may store device or user activity or history as historical data 314. The historical data 314 of a particular user or device may be stored according identification information, such as a user ID or device ID. The historical data 314 may include the viewing patterns or behavior of a user or device, such as the users 308 and 310 and devices 200a and 200b, as well as features of any viewed/accessed content, such as the content's metadata or contextual features (for example, a state of the content and the actual information embedded in the content). In addition, the historical data 314 may include the relationship between metadata or contextual information from a show and how they affect the viewing patterns or behavior of the user or device.

The historical data 314 may include the time or date associated with an accessed content item (such as if a show comes on at 21:00), a particular day of the week associated with a content item (such as if a new episode of a show only comes on Tuesdays), whether there are any exciting moments or events in the content, or other descriptive information for content (such as whether a show is generally a sad, happy, angry show, etc.). Other information that may be included in the historical data 314 may include the name or description of the content item, the content item's platform or channel, content item's location (e.g., IP address), a category/type/classification for the content (such as kids, movie, sports, drama, sitcom, comedy, news, and the like), whether the content is broadcast live, and the like. The historical data 314 may also include which applications the user accesses (such as a news, traffic, weather, shopping, gaming, fantasy sports, or music application) and what time the user accesses those applications.

The historical data 314 may include a schedule describing when or at what times during a period of time (e.g., an hour, day, week, month, year, etc.) a user or device typically accesses/watches content. For example, the historical data 314 may include a schedule detailing which parts of the day the user 308 tends to access or frequently accesses content (such as time periods during the day), and which types of content the user 308 tends to watch or frequently watches during those parts of the day (such as watching kids programming from 16:00 to 17:00). Tending to access content may describe a situation in which the user 308 accesses a content item (e.g., a show, application, etc.) a large part of the time (such as 20%, 50%, 70%, and 90% of the time and the like). The historical data 314 may include different schedules for different time periods, such as a different schedule for each day of the week.

Local office 103 may include a language processing device 316, which may be composed of natural language processing devices, natural language understanding devices, speech recognition devices, and other language processing components/devices. The local office 103 may use the language processing device 316 to extract meaningful information from language queries or inputs (e.g., spoken or text-based). For example, a user 308 may use a microphone input device 208a to input (e.g., speak) the natural language command "change to channel 14." The input device 208a may then transmit this natural language command, via network 311, to the language processing device 316. The language processing device 316 may then process and analyze the command to determine a corresponding output. For example, the language processing device 316 may precisely transcribe the input, and may produce an interpretation/output of "change to channel 14." In another example, the language processing device 316 might not precisely transcribe the input (due to any number of factors, such as distortion, low volume, etc.). In such a case, the language processing device 316 may produce an output that might not fully capture all of the information the user intended with the initial input. For example, when the user 308 says "change to channel 14," the language processing device 316 may produce an output of "beige canal 14." According to some aspects, a user may input information in other ways besides speaking, such as typing, touching, and the like. The language processing device 316 may interpret inputs based on grammar, context, anaphora, user/device history (e.g., the historical data 314), world knowledge, and the like.

Local office 103 may include a mood classification processing device 318. The mood classification processing device 318 may determine a mood state for a user or device and may assign a mood state to a user or device. For example, the language processing device 316 may receive a voice input (e.g., a natural language input) from a user. The language processing device 316 may then produce an interpretation output for that voice input. The mood classification processing device 318 may then analyze or process that output to determine an associated mood state associated with the input or the user or device that transmitted that input. Mood states may comprise happy, unhappy, frustrated, not frustrated, and the like. Mood states will be discussed below in more detail. The local office 103 may then perform actions based on the determined mood state. For example, for an unhappy mood state, the local office 103 may transmit a service or feature for helping the user resolve an issue associated with selecting or accessing content.

Figure 4:
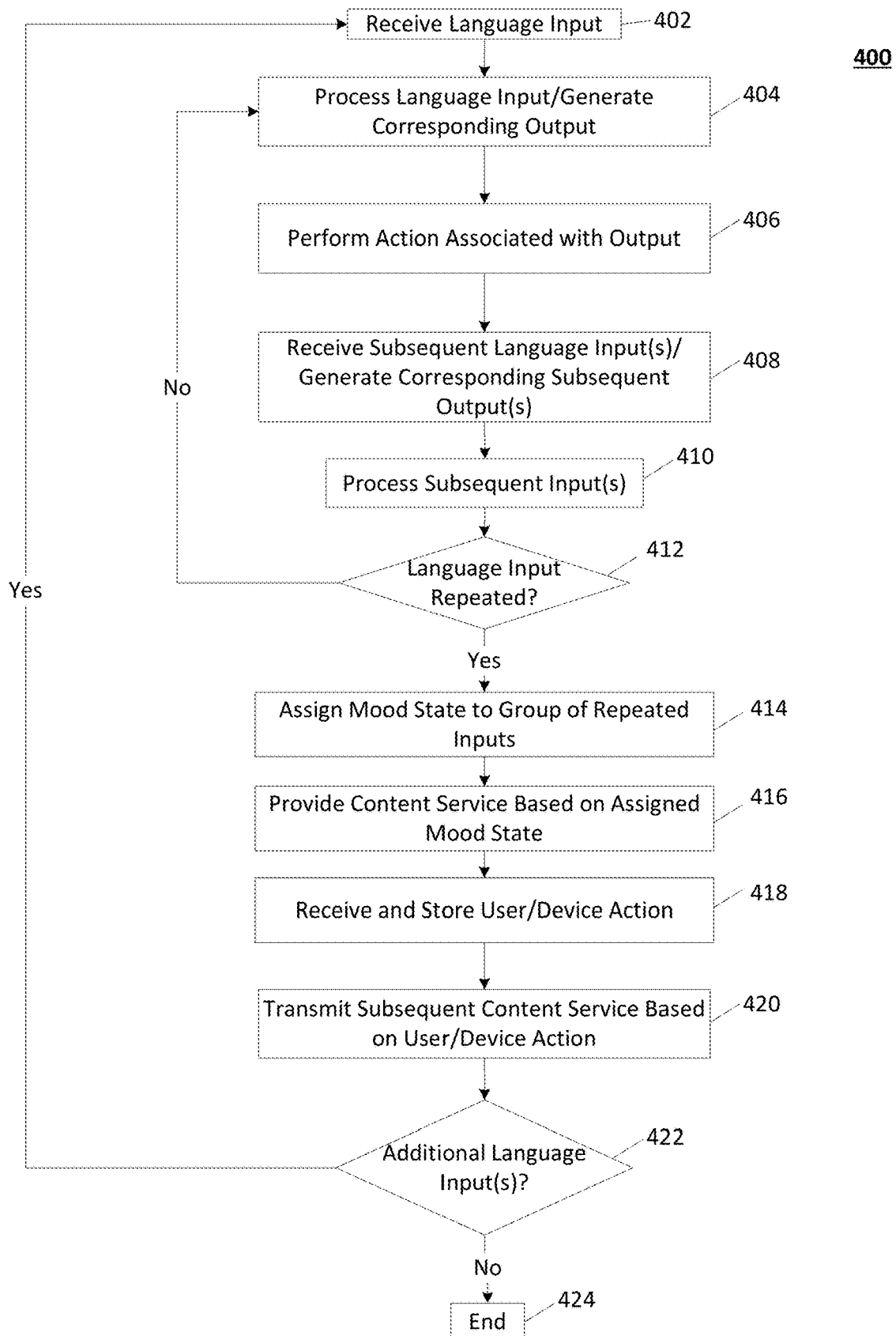
FIG. 4 illustrates an example flow diagram of a method in accordance with aspects of the present disclosure.

FIG. 4 is an exemplary flow diagram illustrating an example process 400 in accordance with one or more disclosed features described herein. In one or more embodiments, the process illustrated in FIG. 4 or one or more steps thereof may be performed by one or more computing devices or entities (e.g., the input devices 208*a* and 208*b*, the computing devices 200*a* and 200*b*, components of the local office 103, one or more content providers, and the like). In other embodiments, the process illustrated in FIG. 4 or one or more steps thereof may be embodied in computer-executable instructions that are stored in a computer-readable medium, such as a non-transitory computer-readable memory. The steps in this flow diagram need not all be performed in the order specified and some steps may be repeated, omitted, or changed in order.

In the example provided, the process 400 may begin with step 402, in which the local office 103 may receive an initial language input from an input device, such as the input device 208*a*, which may be connected to a computing device, such as the computing device 200*a*. For example, the user 308 may speak into a microphone attached to a remote that may control a set-top box (e.g., the device 200*a*) to input a natural language input. The input device 208*a* may transmit this input to the local office 103 via the network 210.

At step 404, the local office 103 may use the language processing device 316 to process and analyze the input received at step 402. According to some aspects, the language processing device 316 may use speech recognition techniques to produce an output (for example, a text based transcription) of the input (for example, natural language speech input). As described above, the language processing device 316 may or may not precisely transcribe an input. For example, for the input "change to channel 14," the language processing device 316 may use speech recognition techniques to produce, in one instance, an output of "beige canal 14." In another instance, the language processing device 316 may produce an output of "change to channel 14," and in another instance, the language processing device 316 may produce an output of "channel 14." Thus, for the same input, the language processing device 316 may produce various different outputs.

In one example, the language processing device 316 may analyze acoustic signals of a speech input. The language processing device 316 may determine a pitch or frequency of the speech input (for example, how high or low a speech signal is). A sex of a person may be determined based on the speech signal. For example, an adult women's voice may typically range between 165 Hz to 255 Hz, an adult male's voice may typically range between 85 Hz to 180 Hz, and a child's voice may typically range between 250 Hz to 300 Hz and higher. The language processing device 316 may determine a frequency for each received speech input, and may determine the sex of a speaker based on the pitch frequency.

According to some aspects, the language processing device 316 may use the historical data 314 to determine an identity of a user. For example, the language processing device 316 may determine users associated with a device (for example, users of an account associated with the device ID), and may retrieve saved speech signal information for the device or users of the device. Based on this speech information, the language processing device 316 may determine that a current speech signal is coming from a particular user associated with that device. Thus, language processing device 316 may distinguish input signals transmitted by a father, a child, or a mother of a family by inspecting the currently received speech signal frequency and previously saved signals. A user may change the frequency of the user's voice, such as when the user sings, when the user yells, when the user groans, and the like. The language processing device 316 may detect such changes in speech frequency or speed.

According to some aspects, a speech signal may be composed of one or more frequencies or harmonics. The language processing device 316 may determine such harmonics using, for example, mel-frequency cepstral modeling to determine mel-frequency cepstral coefficients (MFCCs) for a speech signal/input. The language processing device 316 may use the Fourier transform to determine the MFCCs for a speech signal and determine which frequencies comprise a speech signal. The language processing device 316 may then use the MFCCs to determine an identity of a speaker, and the like.

According to some embodiments, the language processing device 316 may need to process the received input for a period of time before producing an output. For example, the processing time may depend on any of a number factors, such as the complexity of an input, the previous history of a user/speaker, tone of voice, whether the input is a repetition of a previous input, and the like. The language processing device 316 may then save the corresponding processing time for generating an output.

At step 406, the local office 103 may perform an action (or actions) in response to generating an output for the input received at step 402. Depending on the output produced at step 404, the action may comprise transmitting content or a service to device 200*a*, tuning the device to a content item (e.g., a show, application, webpage, etc.), displaying one or more content items on device 200*a*, asking a question via device 200*a*, transmitting a help service to device 200*a*, change of volume, opening an application on the device 200*a*, transmitting an application to the device 200*a*, and the like. According to some aspects, the local office 103 may search content (e.g., content stored/accessed by content server 106) based on the output, such as if the user's input indicated a search request. For example, if the user input the speech command "Blacklist" into an input device, and the language processing device 316 generated an output of "Blacklist," then the local office 103 may search content/content sources for episodes of the Blacklist television show. Alternatively or additionally, the local office 103 may then transmit a list of Blacklist television episodes to device 200*a* or tune device 200*a* to an episode of the Blacklist.

According to some aspects, the local office 103 might not perform an action in response to producing an output. For example, if the output produced at step 404 does not make sense or does not correspond to an action that the local office 103 is capable of performing, then the local office 103 might not perform an action. Alternatively, the local office 103 may transmit a message/question to the device 200*a*, such as "please repeat." Another action that the local office 103 may perform may include browsing. Browsing may include displaying a variety of content item choices on the device 200*a*. For example, the language processing device 316 may produce an output interpretation of "Show me action adventure." Based on this output, the local office 103 may generate a list of action/adventure programs, and transmit this list to device 200a.

At step 408, the local office 103 may receive a second language input from an input device, such as the input device 208a, which may be connected to a computing device, such as the computing device 200a. Step 408 may be similar to step 402. According to some aspects, the local office 103 may receive more than one language inputs at step 408. According to some aspects, if the user does not like the action taken by local office 103, the user may make another input. Additionally, if the user wants to access another content item, then the user may make another input.

According to some aspects, a user/device may generate additional inputs at step 408 in response to receiving or observing the action(s) performed by the local office 103 at step 406. For example, if the user (at step 402) initially input "change to channel 14," but the local office 103 interpreted this to mean "beige canal 14" and subsequently asks the user to repeat the response, the user may then repeat the input "change to channel 14." In another example, if the local office 103 performed no action (e.g., was not capable of performing an action based on the output, was still processing the input received at step 402, etc.), the user may repeat the user's initial input of "change to channel 14." In another example, if the local office 103 tuned the device 200a to channel 4 instead of to channel 14, the user may repeat the command "change to channel 14." In another example, if the local office 103 tuned the device 200a to channel 14, and the user wanted to go to another channel, the user may state "change to channel 55."

At step 410, the local office 103 may use the language processing device 316 to process and analyze the input(s) received at step 408. According to some aspects, the language processing device 316 may use speech recognition techniques to produce an output (e.g., a text based transcription) of the input (e.g., natural language speech input). Step 410 may be similar to step 404.

At step 412, the local office 103 may use the mood classification processing device 318 to determine if the input received at step 402 was repeated in the subsequently received input at step 408. For example, the mood classification processing device 318 may inspect the output produced for each of the inputs and determine whether the any of the outputs match, partially match, substantially match, or correlate to each other. According to some aspects, the outputs may be text-based, such that the mood classification processing device 318 may identify matching terms, words, phrases, numbers, and the like in each output to determine whether one output correlates/corresponds to another output.

The mood classification processing device 318 may determine theses terms, words, phrases, numbers, etc. by determining natural language processing (NLP) entities in the output. For example, an initial output produced at step 404 may be "Cantina the bug guy," and a subsequent output produced at step 410 may be "Canon the bug guy." Thus, these outputs might not precisely match. However, the mood classification processing device 318 may identify entities in these two outputs. The mood classification processing device 318 may identify "Cantina," "bug," and "guy" for the first output, and may identify "Canon," "bug," and "guy" for the second output. The mood classification processing device 318 may then determine a correlation between the identified entities or terms in both of the outputs. For example, both outputs contain the words "bug" and "guy," and thus, the mood classification processing device 318 may determine that there is a match or correlation between these outputs. Accordingly, because of the match between the outputs, the mood classification processing device 318 may determine that the initial input was repeated. Alternatively or additionally, the mood classification processing device 318 may inspect a part of a term, or a syllable of a word, to determine whether outputs match. For example, the words "canon" and "cantina" both begin with the letters "can." Accordingly, the mood classification processing device 318 may determine that there is sufficient correlation between the words "canon" and "cantina" because these words both begin with the letters "can." According to some aspects, more than one subsequent input may be received at step 408. In such situations, after the processing of these inputs at step 410, the mood classification processing device 318 may determine whether the initial input was repeated in any of these subsequent inputs.

After determining that the initial input was repeated, the mood classification processing device 318 may group the repeated inputs or the corresponding outputs together. The mood classification processing device 318 may group the repeated inputs or outputs based on whether the inputs were received within a predetermined period of time. For example, the initial input may be received at 11:08:08, and a repeated subsequent input may be received at 11:08:40, and another repeated subsequent input may be received at 11:08:48. Accordingly, if the predetermined period of time for grouping repeated inputs is one minute, then the mood classification processing device 318 may group these three inputs together into a group or block. According to some aspects, a group of repeated inputs may comprise repeated inputs that were received consecutively. For example, in the above situation, if no other inputs were received between the first input received at 11:08:08 and the last input received at 11:08:48, then the mood classification processing device 318 may generate a group of these three consecutive inputs. If a non-repeated input was received at 11:08:45, then the mood classification processing device 318 may group only the first two inputs into a group that is based on consecutively repeated inputs. According to some aspects, a group of repeated inputs may comprise repeated inputs that were received consecutively or non-consecutively. For example, in the above situation, if a non-repeated input was received at 11:08:45, then the mood classification processing device 318 may still group together the initial input received at 11:08:08, the repeated subsequent input received at 11:08:40, and the repeated subsequent input received at 11:08:48 even though local office 103 received an intervening non-matching input. While one minute was used for the predetermined period of time in the above examples, the mood classification processing device 318 may set the predetermined period of time to any period of time.

In another example, the words "canon" and "cantina" both begin with the letters "can." Accordingly, the mood classification processing device 318 may determine that there is sufficient correlation between the words "canon" and "cantina" because these words both begin with the letters "can." Based on this correlation, the mood classification processing device 318 may determine that the word "cannon" may have been repeated with the input of the word "cantina."

According to some aspects, the mood classification processing device 318 may use acoustic signals of an input to group repeated inputs. For example, the mood classification processing device 318 may group together repeated speech inputs having a similar frequency. For example, a female user 308 of a device 200a may utter a plurality of repeated inputs, and a male user 310 of the device 200a may utter a plurality of repeated inputs. These inputs may overlap one another in time. Accordingly, based on the frequencies of the speech signals, the mood classification processing device 318 may group the female's inputs together in one group and may group the male's inputs together in another group. The mood classification processing device 318 may also group inputs together based on device ID. For example, repeated inputs may be received from a first device (the device 200*a*) and a second device (the device 200*b*). The mood classification processing device 318 may then group the inputs into groups based on associated device IDs for each device that transmitted the inputs.

If the initial input is repeated, the process may continue to step 414. If the initial input is not repeated, then process may return to step 404, or end.

At step 414, the mood classification processing device 318 may assign or determine a mood state to a group or block of repeated inputs. The assigned mood state may be, for example, happy, unhappy, frustrated, not frustrated, sad, angry, excited, and the like. According to some aspects, the assigned mood may be a value within a range of values. For example, the range may comprise the values from 1 to 10, with the value 1, which may represent very happy (or content or not frustrated) and 10, which may represent completely unhappy (or completely frustrated). These values may represent different degrees of a mood, such as happiness or anger. The mood classification processing device 318 may then assign to the group of repeated inputs a value within this range. For example, the mood classification processing device 318 may assign a value of 3, meaning slightly more unhappy than "very happy," but still happy, or a value of 9, meaning slightly below "completely unhappy."

The mood classification device 318 may also assign/determine a mood based on the processing time associated with processing an output for the initial input (step 404). A user may become more frustrated when the language processing device 316 takes a longer time to produce an output for user's initial input. For example, if the user inputs the speech input "Play Michael's song," the language processing device 316 might not know which song to transmit to the user/device, and thus may take a long time to process the input or produce an action for the input. The user may become frustrated or unhappy during this extended processing time period. Accordingly, at step 414, if the processing time for the initial input (or any subsequent matching input) in a group is beyond a threshold time period (for example, a predetermined threshold time period), then the mood classification processing device 318 may assign a mood state associated with frustration, unhappiness, or angriness to that group of inputs.

The mood classification processing device 318 may assign a mood state to a group of inputs based on a frequency of repetition associated with the group of repeated inputs. The mood classification processing device 318 may determine the mood state based on how many repeated subsequent inputs (such as a threshold number) are in the group produced at step 412. For example, if there are not many repeated inputs in the group (e.g., one or two repeated inputs), then the mood classification processing device 318 may assign a mood state associated with happiness or slight unhappiness. If there are many repeated inputs in the group (e.g., three or more repeated inputs), then the mood classification processing device 318 may assign a mood state associated with frustration, unhappiness, very unhappiness.

In another example, the words "canon" and "cantina" both begin with the letters "can." Accordingly, the mood classification processing device 318 may determine that there is sufficient correlation between the words "canon" and "cantina" because these words both begin with the letters "can." Based on this correlation, the mood classification processing device 318 may determine that the word "cannon" may have been repeated with the two inputs of the word "cantina." Based on this determination, the mood classification processing device 318 may determine that the initial input of cannon may have been repeated twice with the two inputs of the word "cantina." In such a case, if a threshold number of subsequent inputs might be set to two repeated subsequent inputs, the mood classification processing device 318 may assign a mood state associated with unhappiness or frustration.

In addition, the mood state may be based on how frequently the initial input is repeated within a predetermined time period. Thus, the mood classification processing device 318 may assign varying degrees of mood based on how many times an input is repeated. For example, if an input is repeated twice within a short period of time (e.g., 6 seconds), then the mood classification processing device 318 may assign a mood state associated with frustration to that group of inputs. In another example, if an input is repeated 8 times within a longer period of time (e.g., 24 hours), then the mood classification processing device 318 may assign a mood state associated with happiness or non-frustration, or may assign no mood state, such as if the user is browsing.

The mood classification processing device 318 may assign a mood state to a group of inputs based on a speed of the speech input (e.g., how fast the user is speaking) or one or more frequencies/pitches that comprise the inputs. For example, a higher frequency pitch may indicate excitement, happiness, contentment, and the like, and a lower frequency pitch may indicate sadness, unhappiness, angriness, and the like. In another example, a fast talking speaker may indicate frustration and the like.

At step 416, the local office 103, based on the assigned mood state, may generate and transmit (or otherwise make accessible or make available) a content item, content feature, or content service to the user 308 or to the device 200*a* that transmitted (or otherwise associated with or connected to) the inputs received at steps 402 and 408. According to some aspects, the local office 103 may provide the content item, content feature, or content service to other devices that might not have transmitted the inputs at steps 402 and 408 (e.g., to the device 200*b*). According to some aspects, the content service may comprise a service for helping the user resolve an issue associated with selection or accessing content. For example, if the assigned mood state is associated with frustration or unhappiness, then the user may be having trouble accessing a show or application, and may have repeated a speech input many times out of frustration. In such cases, the local office 103 may transmit a dialog session (e.g., live chat with customer service), one or more questions to help the local office 103 determine the user's intent or desire, advertisements, and the like. The local office 103 may transmit a list of content items (e.g., shows, applications, etc.) that the local office 103 may have determined to be candidates for the repeated inputs.

According to some aspects, the local office 103 may transmit a content service that may correspond with the assigned/determined mood state. For example, if the mood classification processing device 318 assigns a mood state associated with frustration or anger, then local office 103 may transmit a show or application dealing with or associated with frustration or anger (e.g., a boxing match, boxing video game, etc.).

According to some aspects, the local office 103 may transmit a content service that might not correspond with the assigned mood state. For example, if the mood classification processing device 318 assigns a mood state associated with frustration or anger, then local office 103 may transmit a show or application dealing with or associated with happiness or non-frustration (e.g., an ad showing puppies or kittens, a feel-good movie, etc.). Accordingly, the mood classification processing device 318 may transmit content services that seek to facilitate or counter an assigned mood state.

According to some aspects, the local office 103 may transmit a content service based on determined data associated with a user (e.g., sex, age, etc.). Such a determination may be made based on the pitch of voice or a user/device ID. For example, the local office 103 may determine, based on a pitch frequency of a speech input, that the user is a child. Accordingly, local office 103 may transmit a child-friendly content service to the user/device, such as a children's show, and the like.

According to some aspects, the local office 103 may transmit a content service to a user/device based on the assigned mood and information stored in the historical data 314. For example, the mood classification processing device 318 (or an associated computing device) may have previously assigned a mood state (for example, a mood state associated with frustration) to a user/device. This previous mood state may have been based on received inputs, such as repeated inputs described above and herein. Based on this previous mood state, the local office 103 may have previously transmitted a particular service (for example, a help service) to the user/device. The user/device may have then performed an action in response to receiving this help service. For example, the user/device may have retrieved a content guide (for example, by using an input device) that may have displayed a list of content items (e.g., shows, applications, etc.) from which to select. Accordingly, if now, at step 416, the currently assigned mood state is one that is also associated with frustration (for example, a similar mood state as a previously assigned mood state), then the local office 103 may base the service transmitted at step 416 on the previously assigned mood state. Thus, continuing with the above example, if the currently assigned mood state is associated with frustration, then based on the user's previous action of pulling up a content guide, local office 103 may transmit a content guide to the device/user (or otherwise make the device generate/display a content guide).

At step 418, the local office 103 may store, in the historical data 314, any user/device action or input (for example, subsequent natural language inputs) received from the user (e.g., the user 308) or device (e.g., the device 200a) subsequent to or in response to the content service transmitted by the local office 103 at step 416. According to some aspects, the user may reject or accept/comply with a content service transmitted by the local office 103 at step 416. For example, the local office 103 may transmit one or more questions to the user/device to resolve a possible issue with retrieving/accessing content. The user might not answer the questions, and may, for example, close the question window, pull up a guide screen, make a subsequent input, ignore the question, or the like. In such a case, the local office 103 may identify that the user did not accept the transmitted content service, and may store this information in the historical data 314. The local office 103 may also identify the action taken by the user, and may store this action (along with the assigned mood, user/device ID, etc.) in the historical data 314. The local office 103 may then use this stored information in subsequent situations that correspond with the current situation/mood state (such as those discussed above).

According to some aspects, the stored historical data 314 may be used by the local office 103 when a user uses different devices. For example, the mood classification processing device 318 may assign a mood state to a group of inputs from the user 308 using device(s) 200a and 208a. The user 308 may then make a particular action (e.g., a natural language input, content selection, guide display, application selection, tuning to a cable channel, changing a cable channel, aborting an application or show, etc.) in response to receiving a content service. The local office 103 may store this action and an associated mood state. If the user 308 then makes a series of repeated inputs on device(s) 200b/208b, the local office 103 may determine that the inputs are associated with the user 308 (e.g., via a user ID, pitch frequency, account, etc.), and may assign a same or similar mood state to these inputs. The local office 103 may then retrieve the saved historical data from the user 308 using device(s) 200a/208a, and transmit a content service to the user 308 or device(s) 200b/208b based on this stored historical data (for example, the same or similar content item/service as previously selected by the user).

At step 420, the local office 103 may then transmit a subsequent content service based on the user action received at step 418. If the user tuned the device to a channel, the local office 103 may tune the device that channel. The user/device may have interacted with the service transmitted at step 416, and thus local office 103 may continue to transmit that service to the user/device. For example, the local office 103 may transmit (at step 416) a help related content service to the user/device that asks the user questions. The user may respond by inputting an answer to a question, and then local office 103 may transmit a subsequent question to the user based on the answer to the first question. For example, the local office 103 may ask "What is the matter?" The user may respond "I am having trouble." The local office 103 may then ask "What are you having trouble with?" In some cases, after receiving an answer to a question from a user, the local office 103 may transmit content or another service to the user/device. For example, the user may respond "I want to watch the Oscars" to the question "What are you having trouble with?" The local office 103 may then tune the device to the channel with the Oscars or may transmit the Oscars program to the user.

The user 308 might not answer help related questions, and may, for example, close the question window, pull up a guide screen, make a subsequent input, ignore the question, or the like. Thus, in response to closing the question window, the local office 103 may transmit another service to the user 308. This service may be a service that may be secondary or supplemental to the service transmitted at step 416 and may also be based on the assigned mood state (for example, the mood state from step 414). The supplement service may be a next (e.g., second, third, etc.) highest rated service determined by the local office 103 (for example, the highest rated service may be the service transmitted to the user 308 or the device 200a at step 416). Thus, in response to closing the question window, the local office 103 may, instead of transmitting help related questions, transmit a user guide screen to the user.

In another example, the local office 103 may transmit (at step 416) a dialog session (for example, a live chat with customer service) to the user/device. The local office 103 may use the dialog session to live chat with the user 308 via the device 200a. For example, a representative associated with the local office 103 may ask the user 308 questions or may give instructions to the user 308 regarding how to operate services associated with the device 200a or the local office 103. The dialog session correspondence may go back and forth between the user 308 and the representative. Then, based on the responses from the user 308, the local office 103 may transmit a server to the user. For example, the user 308 may input (e.g., via speech) that the user 308 desired to see a basketball game, and then the local office 103 may transmit the basketball game content to the user 308.

In another example, the local office 103 may transmit, to the user 308, a content item that may be associated with a different type of content. For example, if the local office 103 transmitted, to the user 308, the user's favorite music content item (e.g., favorite song or music video) in response to assigning a mood state associated with frustration or anger (e.g., to help alleviate the anger or frustration), the user 308 may input (e.g., via speech) that the user 308 might not want to listen to that music content (e.g., at step 418). In response, the local office 103 may transmit the user's favorite gaming application to the user (which may also be based on the assigned mood state).

At step 422, local office 103 may determine whether any additional language inputs have been received, and if so, the process may return to step 402. For example, after the local office 103 determines that a predetermined period of time might have passed since a content item or service has been transmitted by the local office 103 to the user 308, or after the local office 103 determines that no inputs may have been received from the user 308 for the predetermined period of time, the local office 103 may determine that the user 308 may be pleased with the provided content service or item. Then, after this predetermined period of time, the user 308 may make another input. For example, the user 308 may have finished watching a television program and may wish to see a guide screen, and thus, may input (for example, via speech) the words "guide screen." In such cases, the process may return to step 402. According to some aspects, if there are no additional language inputs, the process 400 may end at step 424. According to some aspects, the process 400 may end after any step or at any time.

FIG. 5 illustrates 8 example entries for outputs that the language processing device 316 may have generated for 8 inputs (e.g., speech-based inputs) received by the local office 103 that a user 308 may have transmitted. The user may have entered these inputs via the input device 208a or the device 200a. Each entry may comprise an identification code 502 that may be used by components of the local office 103 as a retrieval reference for a particular entry. Each entry may comprise a date and time stamp 504 that may be used by components of the local office 103 as a reference for the date or time that the local office 103 received an input. Each entry may also comprise an output 506 (e.g., a natural language transcription) that the language processing device 316 may have generated for a corresponding input.

As described above, inputs may be grouped together based on whether an input's corresponding output correlates to another input's corresponding output, such as by determining whether terms in the outputs match or partially match. For example, the output for entry 7 comprises the term "400." The outputs for entries 1, 3, 4, 5, and 6 also contain the term "400." The corresponding input for entry 7 was received on Jan. 10, 2014 at 23:16:23, and the corresponding inputs for entries 1, 3, 4, 5, and 6 were received at later times on the same date. Accordingly, the mood classification processing device 318 may determine that the corresponding input for entry 7 may have been repeated by a user by determining that the entries 1, 3, 4, 5, and 6 also contain the term "400" and were input at a later time than entry 7. Thus, the mood classification processing device 318 may group entries 1, 3, 4, 5, 6, and 7 together in a block, and may then determine/assign a mood state to that block in accordance with one or more features described herein.

In another example, the mood classification processing device 318 may group entries 1, 3, 4, 5, 6, 7, and 8 together in a block. In such a situation, the mood classification processing device 318 may determine that entry 8 contains the term "40." The mood classification processing device 318 may also determine that the entries 1, 3, 4, 5, 6, and 7 contain the term "400." The device may then determine that "40" partially matches or correlates to "400" (e.g., because both terms contain "40"), and may then group these entries in a block.

According to some aspects, the mood classification processing device 318 may group entries based on a predetermined time period. For example, the mood classification processing device 318 may group entries 5, 6 and 7 in a first block, and may group entries 3 and 4 together in a second block based on each entry's time stamp. In such a situation, the mood classification processing device 318 may group repeated inputs that are received within 20 seconds of an initial input. In another example, the mood classification processing device 318 may group entries 6, 7, and 8 in a first block, and may group entries 3 and 4 in a second block based on each entry's time stamp. In such a situation, the mood classification processing device 318 may group repeated inputs that are received within 7 seconds of the initial input or a previously repeated input.

Although example embodiments are described above, the various features and steps may be combined, divided, omitted, rearranged, revised or augmented in any desired manner, depending on the specific outcome or application. Various alterations, modifications, and improvements will readily occur to those skilled in art. Such alterations, modifications, and improvements as are made obvious by this disclosure are intended to be part of this description though not expressly stated herein, and are intended to be within the spirit and scope of the disclosure. Accordingly, the foregoing description is by way of example only, and not limiting. This patent is limited only as defined in the following claims and equivalents thereto.

The invention claimed is:

1. A method comprising:
   determining, by a computing device and based on a correlation between two or more terms in one or more natural language inputs, a characteristic associated with the two or more terms;
   determining, based on the characteristic associated with the two or more terms, a mood state associated with the one or more natural language inputs;
   determining, based on the mood state, a content service; and
   causing output of the content service.

2. The method of claim 1, wherein the characteristic comprises at least one of:
   a quantity of terms in the two or more terms;
   a frequency of the two or more terms; or
   a time period associated with the two or more terms.

3. The method of claim 1, wherein the determining the characteristic associated with the two or more terms comprises determining that the two or more terms are repetitions.

4. The method of claim 1, wherein the determining the mood state is further based on one or more of:
   a processing time associated with processing the one or more natural language inputs;

a speed of speech associated with the one or more natural language inputs;

a voice characteristic associated with the one or more natural language inputs; or one or more of: a sex of a user or an age of the user.

5. The method of claim 1, wherein the mood state is associated with a degree of frustration, and wherein the causing output of the content service is based on the degree of frustration.

6. The method of claim 1, further comprising:

after the causing output of the content service, receiving one or more indications of one or more user actions, the one or more user actions comprising a subsequent natural language input; and causing, based on the one or more indications of the one or more user actions, output of a second content service associated with the subsequent natural language input.

7. The method of claim 1, wherein the content service comprises one or more of: a dialog session, one or more questions, media content, an application, or an advertisement.

8. The method of claim 1, wherein:

the mood state comprises one or more of frustration or unhappiness; and wherein the content service comprises a service associated with helping a user resolve an issue associated with accessing content.

9. The method of claim 1, further comprising:

after the causing output of the content service, receiving one or more indications of one or more user actions, wherein the one or more user actions comprise one or more of selecting a content asset, changing from a content asset, accessing an application, aborting an application, or displaying a content guide; and causing, based on the one or more indications of the one or more user actions and further based on one or more second natural language inputs related to the one or more natural language inputs, output of a second content service.

10. The method of claim 1, further comprising:

determining a natural language text-based transcription for the one or more natural language inputs, wherein the correlation comprises:

one or more first terms in the natural language text-based transcription; and one or more second terms in the natural language text-based transcription.

11. A method comprising:

determining, by a computing device, a quantity of occurrences of one or more terms in one or more natural language inputs;

determining, based on the quantity of the occurrences, a mood state associated with the one or more natural language inputs;

determining, based on the mood state, a content service; and causing output of the content service.

12. The method of claim 11, wherein the determining the quantity of the occurrences comprises determining correlations of terms in the one or more natural language inputs.

13. The method of claim 11, wherein the determining the quantity of the occurrences comprises grouping the occurrences of the one or more terms based on at least one of:

a time period associated with the occurrences; or acoustic characteristics associated with the one or more natural language inputs.

14. The method of claim 11, wherein the determining the quantity of the occurrences comprises determining the quantity of the occurrences in a predetermined time period.

15. The method of claim 11, wherein the determining the mood state is further based on one or more of:

a processing time associated with processing the one or more natural language inputs;

a speed of speech associated with the one or more natural language inputs;

a voice characteristic associated with the one or more natural language inputs; or one or more of: a sex of a user or an age of the user.

16. The method of claim 11, further comprising:

after the causing output of the content service, receiving one or more indications of one or more user actions, the one or more user actions comprising a subsequent natural language input; and causing, based on the one or more indications of one or more user actions, output of a second content service associated with the subsequent natural language input.

17. The method of claim 11, wherein the content service comprises one or more of: a dialog session, one or more questions, media content, an application, or an advertisement.

18. The method of claim 11, wherein:

the mood state comprises one or more of frustration or unhappiness; and wherein the content service comprises a service associated with helping a user resolve an issue associated with accessing content.

19. The method of claim 11, further comprising:

after the causing output of the content service, receiving one or more indications of one or more user actions, wherein the one or more user actions comprise one or more of selecting a content asset, changing from a content asset, accessing an application, aborting an application, or displaying a content guide; and causing, based on the one or more indications of the one or more user actions and further based on one or more second natural language inputs related to the one or more natural language inputs, output of a second content service.

20. The method of claim 11, further comprising:

determining a natural language text-based transcription for the one or more natural language inputs, wherein the determining the quantity of occurrences is based on the natural language text-based transcription.

21. An apparatus comprising:

one or more processors; and memory storing instructions that, when executed by the one or more processors, cause the apparatus to:

determine, based on a correlation between two or more terms in one or more natural language inputs, a characteristic associated with the two or more terms;

determine, based on the characteristic associated with the two or more terms, a mood state associated with the one or more natural language inputs;

determine, based on the mood state, a content service; and cause output of the content service.

22. The apparatus of claim 21, wherein the characteristic comprises at least one of:

a quantity of terms in the two or more terms;

a frequency of the two or more terms; or a time period associated with the two or more terms.

23. The apparatus of claim 21, wherein the instructions, when executed by the one or more processors, cause the apparatus to determine the characteristic associated with the two or more terms by causing determining that the two or more terms are repetitions.

24. The apparatus of claim 21, wherein the instructions, when executed by the one or more processors, cause the apparatus to determine the mood state by causing determining the mood state based on one or more of:
   a processing time associated with processing the one or more natural language inputs;
   a speed of speech associated with the one or more natural language inputs;
   a voice characteristic associated with the one or more natural language inputs; or
   one or more of: a sex of a user or an age of the user.

25. The apparatus of claim 21, wherein the mood state is associated with a degree of frustration, and wherein the instructions, when executed by the one or more processors, cause the apparatus to cause output of the content service by causing output of the content service based on the degree of frustration.

26. The apparatus of claim 21, wherein the content service comprises one or more of: a dialog session, one or more questions, media content, an application, or an advertisement.

27. An apparatus comprising:
   one or more processors; and
   memory storing instructions that, when executed by the one or more processors, cause the apparatus to:
      determine a quantity of occurrences of one or more terms in one or more natural language inputs;
      determine, based on the quantity of the occurrences, a mood state associated with the one or more natural language inputs;
      determine, based on the mood state, a content service; and
      cause output of the content service.

28. The apparatus of claim 27, wherein the instructions, when executed by the one or more processors, cause the apparatus to determine the quantity of the occurrences by causing determining correlations of terms in the one or more natural language inputs.

29. The apparatus of claim 27, wherein the instructions, when executed by the one or more processors, cause the apparatus to determine the quantity of the occurrences by causing grouping the occurrences based on at least one of:
   a time period associated with the occurrences; or
   acoustic characteristics associated with the one or more natural language inputs.

30. The apparatus of claim 27, wherein the instructions, when executed by the one or more processors, cause the apparatus to determine the quantity of the occurrences by causing determining the quantity of the occurrences in a predetermined time period.

31. The apparatus of claim 27, wherein the instructions, when executed by the one or more processors, cause the apparatus to determine the mood state by causing determining the mood state based on one or more of:
   a processing time associated with processing the one or more natural language inputs;
   a speed of speech associated with the one or more natural language inputs;
   a voice characteristic associated with the one or more natural language inputs; or
   one or more of: a sex of a user or an age of the user.

32. The apparatus of claim 27, wherein the content service comprises one or more of: a dialog session, one or more questions, media content, an application, or an advertisement.

33. A non-transitory computer readable medium storing instructions that, when executed, cause:
   determining, based on a correlation between two or more terms in one or more natural language inputs, a characteristic associated with the two or more terms;
   determining, based on the characteristic associated with the two or more terms, a mood state associated with the one or more natural language inputs;
   determining, based on the mood state, a content service; and
   outputting of the content service.

34. The non-transitory computer readable medium of claim 33, wherein the characteristic comprises at least one of:
   a quantity of terms in the two or more terms;
   a frequency of the two or more terms; or
   a time period associated with the two or more terms.

35. The non-transitory computer readable medium of claim 33, wherein the instructions, when executed, cause the determining the characteristic associated with the two or more terms by causing determining that the two or more terms are repetitions.

36. The non-transitory computer readable medium of claim 33, wherein the instructions, when executed, cause the determining the mood state by causing determining the mood state based on one or more of:
   a processing time associated with processing the one or more natural language inputs;
   a speed of speech associated with the one or more natural language inputs;
   a voice characteristic associated with the one or more natural language inputs; or
   one or more of: a sex of a user or an age of the user.

37. The non-transitory computer readable medium of claim 33, wherein the mood state is associated with a degree of frustration, and wherein the instructions, when executed, cause the outputting of the content service by causing outputting of the content service based on the degree of frustration.

38. The non-transitory computer readable medium of claim 33, wherein the content service comprises one or more of: a dialog session, one or more questions, media content, an application, or an advertisement.

39. A non-transitory computer readable medium storing instructions that, when executed, cause:
   determining a quantity of occurrences of one or more terms in one or more natural language inputs;
   determining, based on the quantity of the occurrences, a mood state associated with the one or more natural language inputs;
   determining, based on the mood state, a content service; and
   outputting of the content service.

40. The non-transitory computer readable medium of claim 39, wherein the instructions, when executed, cause the determining the quantity of the occurrences by causing determining correlations of terms in the one or more natural language inputs.

41. The non-transitory computer readable medium of claim 39, wherein the instructions, when executed, cause the determining the quantity of the occurrences by causing grouping the occurrences based on at least one of:
   a time period associated with the occurrences; or acoustic characteristics associated with the one or more natural language inputs.

42. The non-transitory computer readable medium of claim 39, wherein the instructions, when executed, cause the determining the quantity of the occurrences by causing determining the quantity of the occurrences in a predetermined time period.

43. The non-transitory computer readable medium of claim 39, wherein the instructions, when executed, cause the determining the mood state by causing determining the mood state based on one or more of:
- a processing time associated with processing the one or more natural language inputs;
- a speed of speech associated with the one or more natural language inputs;
- a voice characteristic associated with the one or more natural language inputs; or
- one or more of: a sex of a user or an age of the user.

44. The non-transitory computer readable medium of claim 39, wherein the content service comprises one or more of: a dialog session, one or more questions, media content, an application, or an advertisement.

\* \* \* \* \*

UNITED STATES PATENT AND TRADEMARK OFFICE
CERTIFICATE OF CORRECTION

PATENT NO. : 11,497,424 B2
APPLICATION NO. : 17/081574
DATED : November 15, 2022
INVENTOR(S) : Des Jardins et al.

It is certified that error appears in the above-identified patent and that said Letters Patent is hereby corrected as shown below:

In the Specification

Column 12, Detailed Description, Line 67:
Delete "200$a$" and insert --200$b$-- therefor Signed and Sealed this
Twenty-sixth Day of December, 2023

Katherine Kelly Vidal
*Director of the United States Patent and Trademark Office*